US009883869B2

(12) United States Patent
Dijkstra et al.

(10) Patent No.: US 9,883,869 B2
(45) Date of Patent: Feb. 6, 2018

(54) TOOL HEAD ASSEMBLY AND ASSOCIATED APPARATUS

(71) Applicant: ACADEMISCH ZIEKENHUIS LEIDEN, Leiden (NL)

(72) Inventors: Pieter Durk Sander Dijkstra, Leiden (NL); Pieter Bakkenes, Leiden (NL); Jesse Pieter Blok, Haarlem (NL)

(73) Assignee: ACADEMISCH ZIEKENHUIS LEIDEN, Leiden (NL)

( * ) Notice: Subject to any disclaimer, the term of this patent is extended or adjusted under 35 U.S.C. 154(b) by 35 days.

(21) Appl. No.: 15/035,974

(22) PCT Filed: Nov. 11, 2014

(86) PCT No.: PCT/EP2014/074276
§ 371 (c)(1),
(2) Date: May 11, 2016

(87) PCT Pub. No.: WO2015/067821
PCT Pub. Date: May 14, 2015

(65) Prior Publication Data
US 2016/0270796 A1 Sep. 22, 2016

(30) Foreign Application Priority Data
Nov. 11, 2013 (GB) .................................. 1319811.4

(51) Int. Cl.
*A61B 17/14* (2006.01)
*A61B 17/16* (2006.01)
*B23D 53/12* (2006.01)

(52) U.S. Cl.
CPC ........ *A61B 17/149* (2016.11); *A61B 17/1637* (2013.01); *B23D 53/12* (2013.01)

(58) Field of Classification Search
CPC .... A61B 17/149; A61B 17/1637; B23D 53/12
See application file for complete search history.

(56) References Cited

U.S. PATENT DOCUMENTS 822,056 A * 5/1906 knox .................... B23D 53/005
144/34.1
1,374,638 A * 4/1921 De Cew ................. B23D 53/12
30/272.1

(Continued)

FOREIGN PATENT DOCUMENTS

| CN | 201798775 U | 4/2011 |
| DE | 2660077 B1 | 8/1978 |
| WO | 2012/170459 A2 | 12/2012 |

OTHER PUBLICATIONS

Response filed Nov. 30, 2016 in related European Patent Application No. 14796501.6, 9 pages.

(Continued)

*Primary Examiner* — Sean Michalski
(74) *Attorney, Agent, or Firm* — Senniger Powers LLP

(57) ABSTRACT

A tool head assembly for a hand held tool The assembly includes a body for attaching to the hand held tool; a continuous cutting band having a cutting edge for cutting into a subject; at least one tension member coupled to the body for holding the cutting band under tension; and at least one drive member coupled to the body for rotating the cutting band with respect to the body.

20 Claims, 6 Drawing Sheets

(56) References Cited

U.S. PATENT DOCUMENTS

| | | | | |
|---|---|---|---|---|
| 2,015,339 | A | * | 9/1935 | Ellingham .......... B23B 51/0406 408/199 |
| 3,267,975 | A | * | 8/1966 | Enders ................ B23B 51/0473 144/23 |
| 4,001,937 | A | * | 1/1977 | Stelljes .................. B23D 53/12 30/380 |
| 4,953,295 | A | * | 9/1990 | Barradas ................ B23D 53/12 30/380 |
| 5,306,285 | A | * | 4/1994 | Miller .................. B23D 61/006 30/355 |
| 5,509,206 | A | * | 4/1996 | Rowe .................. B23D 53/005 30/380 |
| 5,725,530 | A | * | 3/1998 | Popken .................. A61B 17/15 30/166.3 |
| 5,876,405 | A | | 3/1999 | Del Rio et al. |
| 6,089,867 | A | * | 7/2000 | Filho .................. A61B 17/1637 433/175 |
| 6,267,594 | B1 | | 7/2001 | Burkhard |
| 7,918,849 | B2 | * | 4/2011 | Bleich ................ A61B 17/1659 606/1 |
| 8,062,298 | B2 | * | 11/2011 | Schmitz ........... A61B 17/00234 606/79 |
| 2008/0115367 | A1 | | 5/2008 | Glynn |
| 2011/0296696 | A1 | * | 12/2011 | Holly ..................... B23D 53/12 30/380 |
| 2016/0206326 | A1 | * | 7/2016 | Gilhooley ............. A61F 2/4609 |
| 2016/0345987 | A1 | * | 12/2016 | Guilloux ............ A61B 17/1635 |

OTHER PUBLICATIONS

International Search Report and Written Opinion dated Mar. 20, 2015 in related PCT Application PCT/EP2014/074276, 17 pages.
Search Report dated Jun. 12, 2014 in related application GB 1319711.4, 4 pages.
Large Bone Power Products Catalog, Linvatec A CONMED Company, www.linvatec.com, 82 pages.

* cited by examiner

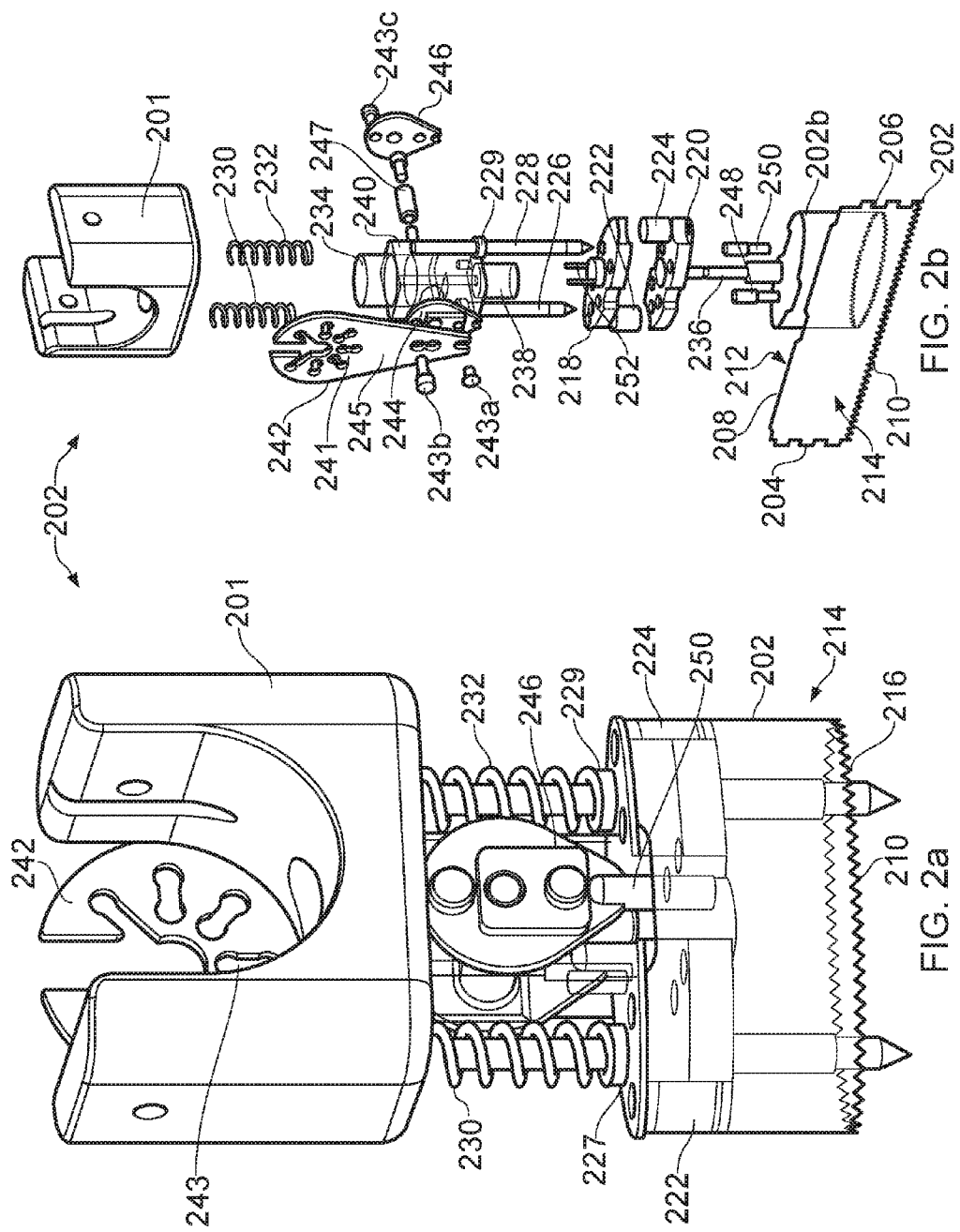

TOOL HEAD ASSEMBLY AND ASSOCIATED APPARATUS

REFERENCE TO RELATED APPLICATIONS

This application is the 371 National Stage Application based on International PCT Application No. PCT/EP2014/074276, filed Nov. 11, 2014, which claims priority to Great Britain Patent Application No. 1319811.4, filed Nov. 11, 2013, both of which are hereby incorporated by reference in their respective entireties.

The disclosure relates to a tool head assembly and, in particular although not exclusively, to medical tool such as a drill or saw head assembly for making an elliptical hole in a subject.

Orthopedic surgical procedures for treating chondrosarcoma involve removing a core, or slab, of cortical bone material from the femur of a patient. After removal of the slab of cortical material there is room to scrape (curettage) chondrosarcoma (with spongeosa) away from the bone. The curettage is done manually and is often guided by previous X-ray evaluations.

The current approach for removal of chondrosarcoma is to saw a square hole (cortical defect) or mill a hole with an unguided tool in the cortical bone. The hole is made just above the central chondrosarcoma. It takes a lot of time and a highly skilled surgeon to make a suitable series of cuts. Each orthopaedic surgeon generally has their own way of preparing a cortical defect. Two or more tools may be required to complete the task. For example, several holes may be drilled with a first tool and then material may be sawed away between the holes using a second tool. In some procedures, such as a craniotomy, a high level of manual dexterity is required of the surgeon to guide the second tool to cut the precise shape required. The selection of tools, such as an oscillating saw, a mill, a chisel or a composition for performing the procedure is typically determined by the surgeon during the intervention procedure.

The shape of the cortical created in the procedure can lead to post-operative fracture because each of the current used shapes and methods for preparing the defect result in the occurrence of stress risers in the bone. The most common load resulting in fracture is a torsion related movement, like rotating a leg during bed rest. Such a motion can cause a fracture along the defect.

Further, central chondrosarcoma can be difficult to reach during curettage of the distal part of the human femur, leading to difficulties and non-uniformities in defect preparation. The avoidance of stress risers is of high importance since there is no way to predict the risk of pathological fractures resulting from the surgical intervention.

After treatment is complete, it is advantageous to replace the removed bone in its original position. It is also important that bone material of the core or the surrounding area should not be lost or damaged during the initial intervention, which can be difficult to achieve using prior art surgical techniques.

According to a first aspect of the invention there is provided a tool head assembly for a hand held tool, the assembly comprising:
- a body for attaching to the hand held tool;
- a continuous cutting band having a cutting edge for cutting into a subject;
- at least one tension member coupled to the body and configured to hold the cutting band under tension; and
- at least one drive member coupled to the body and configured to rotate the cutting band with respect to the body.

The cutting edge of the continuous cutting band can be used to produce a defect in a subject that has a continuous, curved edge, which has been shown to result in less mechanical stress being imparted to the subject and the removed piece. The application of the cutting edge to a subject also results in a uniform hole shape for each use. As such, the use of the tool head assembly can require less skill or effort on the part of the operator in order to produce a known result. The shape of the cutting band and therefore the hole that it cuts in the subject is defined by the tension members, thus providing greater certainty of results.

Cutting a smooth shape free of irregularities reduces the incidence of stress risers. The cutting band may be configured to follow an oval or elliptical path. Oval, or elliptical shaped holes have been shown to further reduce the stress imparted in the subject.

The cutting edge may be disposed in a cutting plane. The entirety of the cutting edge may be exposed. The entirety of the cutting edge may be exposed simultaneously during operating of the tool head assembly. The tool head assembly may have an operating configuration in which the cutting edge is exposed and a retracted configuration in which the cutting edge is within the body or otherwise shielded from a user. During operation, the exposed cutting edge can be brought down on the subject in order to saw a hole into the subject, where all points of the outline of the hole are cut substantially simultaneously. Such a mode of operation results in less skill being required to operate the device whilst providing uniform and consistent results.

The cutting edge may be continuous. The cutting band may be flexible when not under tension. The cutting edge may have a thickness less than 0.2 mm, such as 0.15 mm. Due to the form of the cutting band, the thickness of the cutting edge can be reduced compared to prior art blades where a greater stiffness is required of the blades. In this case, the requirement for such stiffness is reduced, at least in part, by the provision of the tension member. The provision of a thinner blade enables a reduced mismatch between a removed slab and a remainder of the subject and also can reduce damage to the subject due to reduced heat generation by the cutting edge.

The cutting band may be removable and replaceable. The at least one tension member may be movable between a first position in which the band holds the cutting band under tension and a second position in which the band is not held under tension. The at least one tension member may be movable between a first position in which the cutting band is held under tension and a second position in which the cutting band is not held under tension. The cutting band may be removable when the tension member is in the second position. The cutting band may be fixed in the tool head assembly when in the first position and removable from the tool head assembly when in the second position. For clinical applications, it is desirable for the cutting blade to be readily replaceable for hygiene reasons.

The tool head assembly may comprise a guidance assembly for retractably engaging with the subject and/or maintaining a fixed lateral relationship between the cutting band and the subject. The guidance assembly may comprise guidance pins. The guidance pins may extend from the at least one drive member. The guidance assembly may comprise guide rails. The guide rails may extend on either side of the cutting band. The provision of a guidance assembly reduces the probability of damaging the subject due to stray sawing by the cutting band.

The guidance assembly may comprise grooves. The grooves may extend on either side of the cutting band. The grooves may be configured to engage with the subject and/or maintain a fixed lateral relationship between the cutting band and the subject.

The guidance assembly may be configured to interact with the body to form a gauge for providing an indication of a level of retraction of the guidance assembly with respect to the body.

The guidance assembly may be integrated with a sleeve which extends around the body. The sleeve may form a handle for a user. An exterior surface of the sleeve may be ergonomically shaped for ease of use.

The guidance assembly may be configured to define a cutting path of the cutting band. The cutting band may conform to a shape of the guidance assembly.

The at least one cutting band tension member may be integrated with the at least one drive member. The tool head assembly may comprise a plurality of drive members. Each drive member may be in contact with the cutting band. The tool head assembly may comprise a plurality of tension members. Each tension member may comprise a roller that is engageable with, and/or configured to apply a force to, an inner surface of the cutting band in order to hold the cutting band in the tool head assembly. One of the plurality of tension members may be displaceable towards another of the tension member in order to relieve the force applied to the inner surface of the cutting band so that the cutting band may be removed from the tool head assembly.

The tool head assembly may comprise a first drive member and a second drive member. The first drive member may be configured to receive a torque. The first drive member may be configured to transfer at least a portion of the torque to both the second drive member and the cutting band. The first drive member and the second drive member may both contact the cutting band to transfer torque thereto.

The tool head assembly may be an oscillating saw head assembly. The tool head assembly may be configured to receive force from an oscillating driving force and impart an oscillatory motion on the cutting band.

The tool head assembly may be a hand held tool head assembly and/or a drill head assembly. The tool head assembly may be a medical tool head assembly. The cutting edge may be suitable for cutting human or animal bone. The cutting edge may comprise symmetrical teeth.

The tool head assembly may be suitable for a power hand tool. The tool head assembly may be an attachment for a power hand tool. The at least one drive member may be configured to receive torque from a driving force unit of the hand tool. The driving force unit may comprise a motor of a power hand tool.

The tool head assembly may be a completely mechanical cutting tool. The shape of a hole produced by the tool head assembly may be mechanically defined, rather than by means of software or electronics, for example. The use of a completely mechanical cutting tool minimises the risk of malfunctions or negative effects to surrounding tissues such as the iliotibial band, which may be inherent in other cutting techniques.

According to a second aspect of the invention there is provided a cutting band for a tool head assembly of the first aspect, the cutting band comprising a continuous cutting edge for cutting a subject.

According to a third aspect of the invention there is provided a drill or saw comprising the tool head assembly of the first aspect.

Embodiments of the invention will now be described by way of example and with reference to the accompanying drawings in which:

FIG. 2a illustrates an oscillating saw head assembly for receiving an oscillatory driving force;

FIG. 2b illustrates an exploded schematic of the oscillating saw head assembly illustrated in FIG. 2a;

FIG. 3a illustrates an exploded schematic of a drill head assembly for receiving an continuous rotational driving force;

FIG. 3b illustrates another exploded schematic of the drill head assembly illustrated in FIG. 3a;

FIG. 4b illustrates an exploded perspective view of an internal mechanism of the drill head assembly of FIG. 4a;

FIG. 4c illustrates a schematic cross section taken through the drill head assembly of FIG. 4a;

FIG. 5b illustrates another view of the saw of FIG. 5a; and

FIG. 5c illustrates another view of the tool head assembly of FIG. 5a.

FIGS. 2a to 5c show examples of a tool head assembly 200, 300, 400, 502, embodiments of which may be affixed to a drill mechanism or a saw mechanism. The tool head assembly may therefore be considered to be an attachment for a power hand tool.

The tool head assembly comprises a cutting band for cutting a subject. The tool head assembly may be suitable for orthopaedic use where an oval shaped hole in a bone or other form of hard tissue is required. Embodiments of the invention can be used to cut a hole in a subject and produce a replaceable slab. For clinical applications, the cutting blade should be discarded after every procedure. As such, it is desirable for the cutting band to be removable and replaceable.

Figure 1:
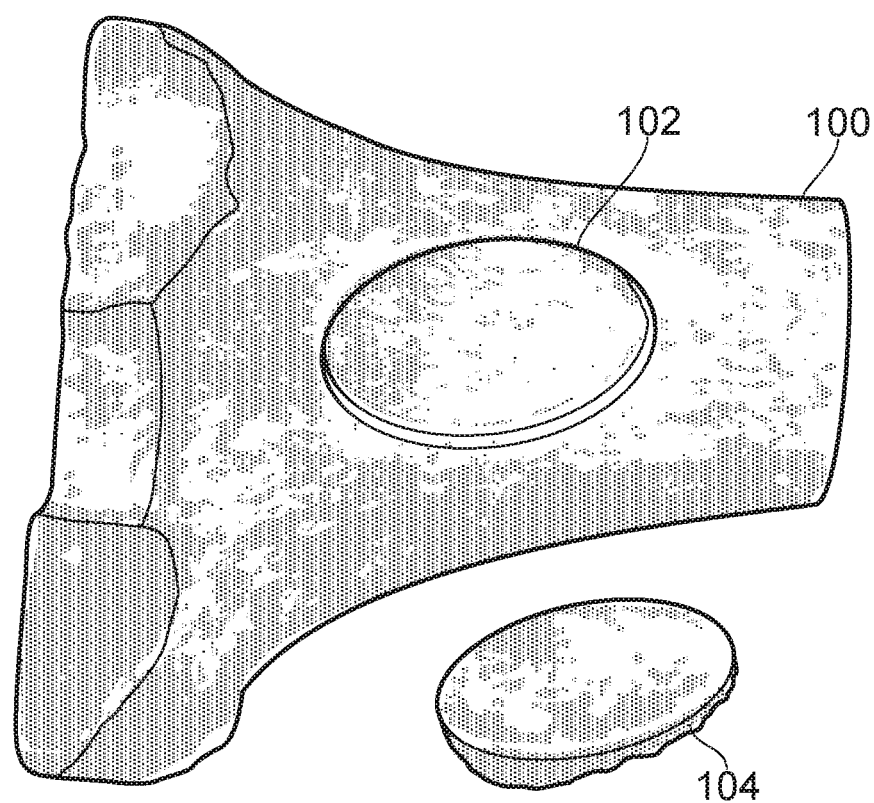
FIG. 1 illustrates a subject with a hole produced by a tool head assembly.

FIG. 1 illustrates a bone 100 which has been the subject of a cut from the tool head assembly. An oval hole 102 has been prepared in the bone 100 and a corresponding slab 104, or core, which has been removed from the hole 102 is shown. Due to the structure of bone, there is a low adherence between the inner spongeosa material shown in the hole 102 and the outer cortical material of which the slab 104 is formed once the outer material has been cut through. The oval slab of cortical bone generated by the cutting can therefore be removed from the spongeosa by a small amount of tension or shear force.

The thickness of the cutting band can be chosen such that the mismatch between the hole 102 and the slab 104 can be minimised so that the slab 104 can be replaced in the hole 102 after a procedure has been completed.

The oval shape of the hole 102 has significant benefits over conventional orthopaedic hole preparations in that the stress resulting from torsion of the bone is reduced. The oval shape of the slab also results in it being stronger than conventional replaceable slabs. Indeed, the possible reduction in such stress in holes produced by the tool head assemblies described herein has been calculated as 55%±10% compared to a conventional defect preparation technique.

Although this disclosure predominantly relates to surgical use, and specifically to orthopaedic use, it will be appreciated that a tool for creating oval or elliptical holes (which result in a lower stress field in the subject) will be of use in a diverse variety of fields such as, for example, horology or forensic testing.

The mechanism of force transfer used to drive the tool head assembly can be varied. For example, the rotation of the cutting band may be continuous or oscillatory. At least one drive member is provided in order to transfer torque form the driving force, such as an oscillatory saw or a drill, to the cutting band.

Two examples of drive member configurations are described below with reference to FIGS. 2a, 2b, 3a and 3b. FIGS. 2a, 2b, 2c and 2d illustrate tool head assemblies for receiving an oscillatory driving force. The same reference numerals are used to refer to corresponding features in FIGS. 2a to 2d. FIGS. 3a and 3b illustrate a tool head assembly for receiving a continuous rotational driving force.

A perspective view of a tool head assembly 200 for receiving an oscillatory driving force is illustrated in FIG. 2a. An exploded perspective view of the tool head assembly 200 is illustrated in FIG. 2b. An advantage of providing oscillatory motion compared to continuous motion is that oscillatory motion can be used to cut hard tissue whilst leaving soft tissue largely undisturbed.

The tool head assembly 200 comprises a main housing 201 for mounting the assembly tool and a cutting band 202. In this example, the cutting band 202 comprises a cutting blade that has a connecting means, such as interlocking features, to attach a first end of the blade 204 to a second end 206 in order to form a continuous band. Alternatively, the cutting band 202 may be pre-formed as a continuous band of material in order to remove the need for the secure connecting means.

The cutting band 202 has an inward facing edge 208 and an opposing outward facing edge 210. The inward facing edge 208 is disposed towards the main housing 201. The outward facing edge 210 may also be referred to as a cutting edge because it has teeth 216 and so provides a cutting blade. The outward facing edge 210 is exposed to allow a subject to be cut by the cutting band 202.

The cutting band 216 is provided with a degree of flexibility in order to allow it to rotate along an elliptical cutting path. However, the cutting band 216 is rigid enough to allow the cutting edge to cut through the subject. A spring steel provides a suitable level of flexibility for bone cutting applications.

The teeth 216 are provided around the entirety of the cutting edge in this example; that is, the cutting edge is continuous. The spacing of the teeth 216 may be configured to providing an efficient cutting edge for the subject while remaining clear of debris during operation. Symmetrical teeth have been found to provide a good cutting action for some applications. The desired spacing of the teeth may also depend on the type of material that the tool head assembly is intended to cut, such as bone, metal, plastic or wood, for example.

The cutting band 202 also has an inner surface 212 and an opposing outer surface 214, each of which is disposed between the inward facing edge 208 and the outward facing edge 210.

During operation, the cutting edge 202 occupies a cutting plane (normal to an axial direction) that can be brought into contact with the subject in order to saw a hole into the subject, such as that illustrated in FIG. 1. All points of the outline of the hole are cut substantially simultaneously. Such a mode of operation results in less skill being required to operate the device whilst providing uniform results. Providing an assembly 200 that can form the hole in a single action, where the body 201 of the assembly 200 remains stationary relative to the subject and the cutting band forms the hole, rather than by numerous cuts or unguided movement of a milling tool, is advantageous.

First and second housing sub-assemblies 218, 220 and first and second tension members 222, 224 are provided for applying tension to the cutting band 202. The first and second housing sub-assemblies 218, 220 each have a moulded elliptical shape and are configured to interlock with one another in the axial direction so as to partially encompass the first and second tension members 222, 224. The tension members 222, 224 interacts with the inner surface 212 of the cutting band 202 in order to hold the cutting band 202 firmly under tension. The first and second tension members 222, 224 each comprise a roller in this example. The rollers each have an axis that extends in the axial direction. The rollers are arranged on opposing sides of, and face outwardly from, the assembled first and second housing sub-assemblies 218, 220. The rollers are in direct rolling contact with the inner surface 212 of the cutting band 202 and impart a frictional force upon the inner surface 212. In this example, sides of the housing sub-assemblies 218, 220 are also in direct contact with the cutting band 202 and so impart tensional and frictional forces on the cutting band 202. The housing sub-assemblies 218, 220 and the rollers are coupled to one another and have a fixed relationship, in the axial direction, with the cutting band 202 in this example. The tightening and untightening of the first and second housing sub-assemblies 218, 220 enables the cutting band 202 to be removed and replaced, as described further below.

Coolant may be provided through small channels (not shown) between the first and second housing sub-assemblies 218, 220. The coolant ensures that heat generated by the cutting band 202 is dissipated so that damage to the subject around the cutting site is reduced.

A guidance assembly prevents lateral movement of the subject relative to the assembly 200 as the cutting band 202 is engaged. The guidance assembly comprises first and second guidance pins 226, 228 that extend in the axial direction through apertures in the first and second housing sub-assemblies 218, 220 towards the subject (away from the main body 201). The first and second guidance pins 226, 228 have retaining portions 227, 229 that extend normal to the pin axes. Springs 230, 232 are provided along the respective axes of the first and second guidance pins 226, 228 and provide a biasing force on the retaining portions 227, 229 relative to the main housing 201. The effect of this biasing force is that a free pointed end of each of the guidance pins 226, 228 protrudes from the assembly 200 through the cutting plane so as to engage with the subject.

The guidance pins 226, 228 are the first portions of the assembly 200 to interact with the surface of the subject when the assembly is in use. The pointed ends of the guidance pins 226, 228 may dig into the subject to an extent. The application of a further downward force on the assembly, that is, a force urging it towards the subject, causes the guidance pins 226, 228 to retract towards the housing and allow the cutting band 202 to engage with the surface of the subject. The guidance pins 226, 228 prevent lateral movement of the subject relative to the assembly 200 while the cutting band 202 is engaged with the subject.

Figure 2C:
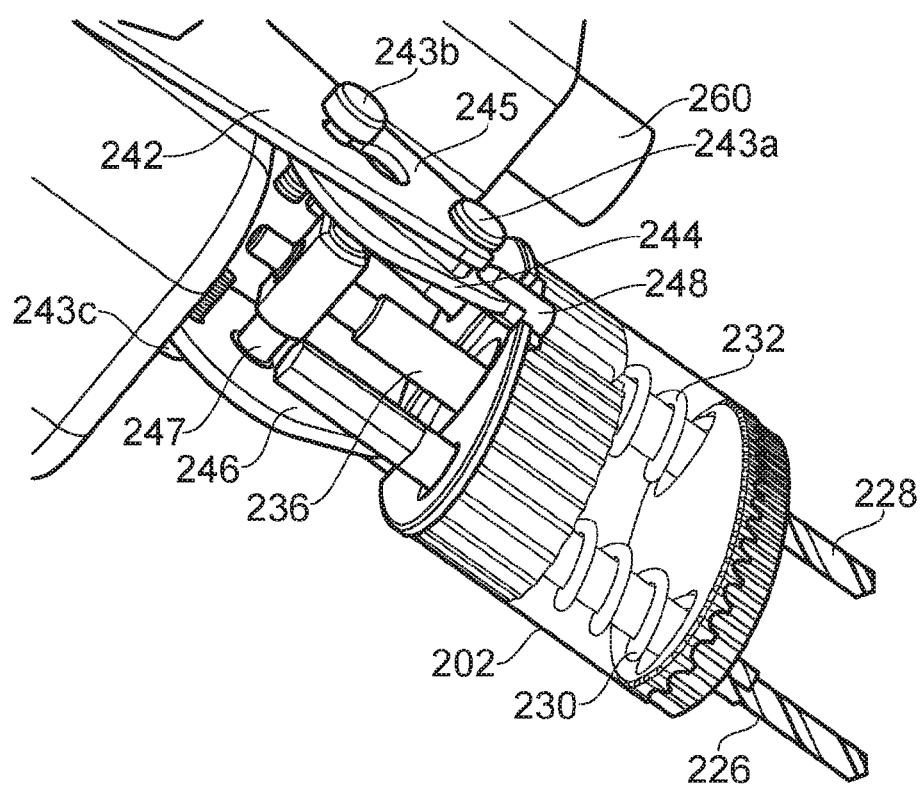
FIG. 2c illustrates a perspective view of a portion of an oscillating saw head assembly similar to that illustrated in FIGS. 2a and 2b.
Figures 3A, 3B:
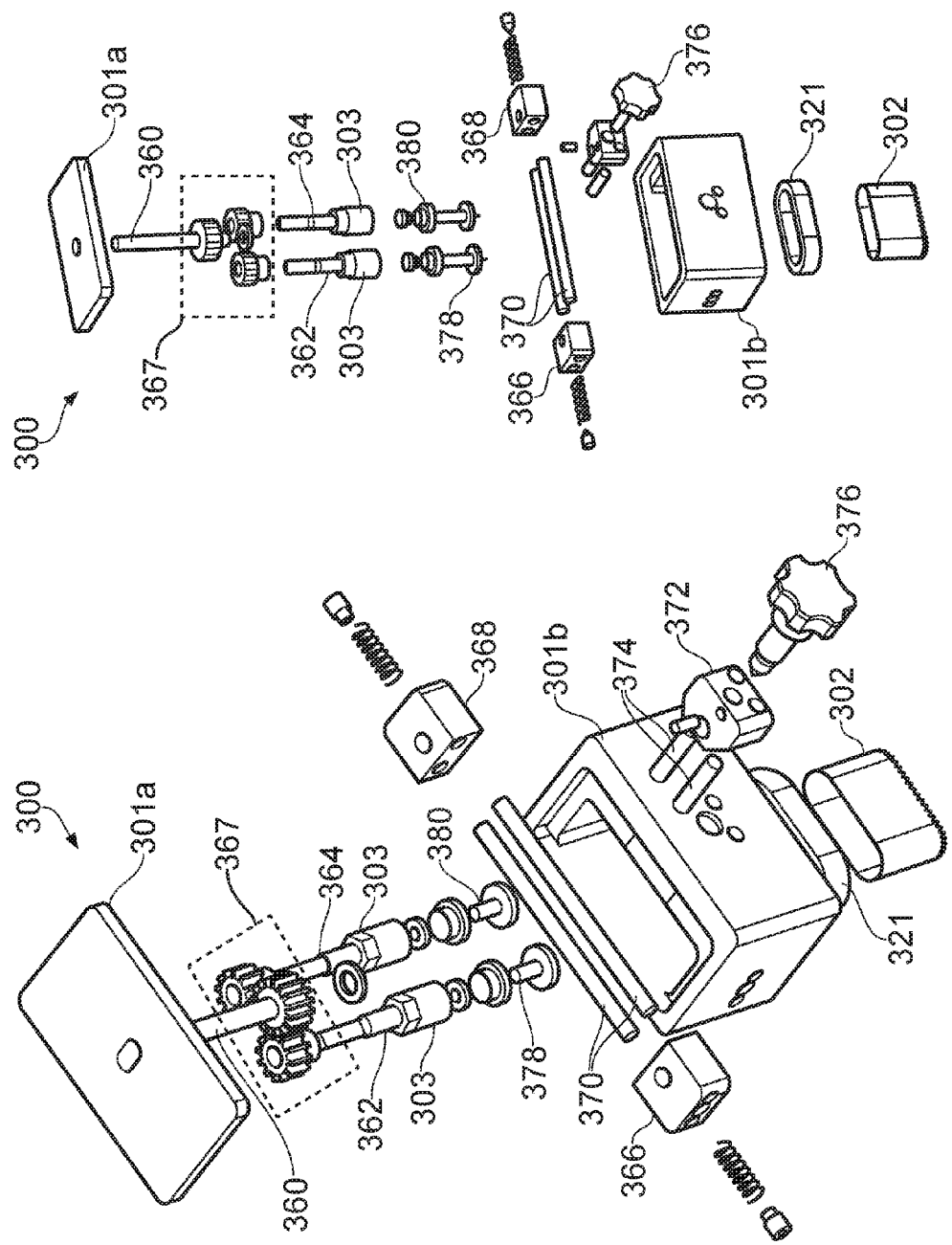

In the example shown in FIG. 2c, the first and second guidance pins 226, 228 of the guidance assembly are provided by drill bits mounted in the first and second housing sub-assemblies 218, 220.

The main body 201 comprises oscillatory motion transfer apparatus. The oscillatory motion transfer apparatus is configured to receive an oscillatory motion from a drive mechanism, such as an oscillatory saw, and transmit that oscillatory motion to the cutting band 202. The oscillatory motion transfer apparatus comprises a main cam 242, first and second sub-cams 244, 246 and associated first and second extension members 248, 250.

The main cam 242 is configured in this example to engage with the head of a conventional oscillatory saw, such as the Hall series 4 oscillating saw. The Hall series 4 oscillating saw produces an oscillating motion at a frequency of 233 Hz with a typical angular displacement of 5 degrees. The main cam 242 has a slot arrangement 241 that is arranged to engage with the driving member of the saw so that an oscillatory motion can be imparted on the main cam 242. The main cam 242 has a distended part 245 that extends radially away from the pivot of the main cam 242 for driving the first sub-cam 244.

The first sub-cam 244 is connected to the main cam 242 by a distal connecting pin 243a. The first sub-cam 244 is pivotally connected by a proximal connecting pin 243b to the sub-assembly 240 of the housing 201. The proximal connecting pin 243b also passes through a slit in the main cam 242, allowing the main cam 242 to move back and forth with respect to the proximal connecting pin 243b. In this way, the main cam 242 can drive the first sub-cam 244 via the distal connecting pin 243a such that the first sub-cam 244 swivels back and forth about the proximal connecting pin 243b.

The second sub-cam 246 has a corresponding proximal connecting pin 243c by which it can swivel with respect to the housing 201. The proximal connecting pins 243b, 243c of the first and second sub-cams 244, 246 are co-axial.

The arrangement of the first and second sub-cams 244, 246 is further illustrated in FIG. 2c (the sub-assembly 240 is not shown in FIG. 2c). The first and second sub-cams 244, 246 are each co-axially and pivotally mounted to a pin assembly 247 that extends between the first and second sub-cams 244, 246. The axis of the pivot between the pin assembly 247 and the first and second sub-cams 244, 246 is normal to an axis of the pin assembly 247.

The pin assembly 247 has opposing first and second ends and a central portion. The first end of the pin assembly 247 is coupled to the first sub-cam 244 at a position between the distal connecting pin 243a and the proximal connecting pin 243b so that side-ways oscillatory motion of the first sub-cam 244 is translated to the pin assembly 247. The central portion of the pin assembly 247 is pivotally coupled to a bolt 236 of the housing that extends in the axial direction. In this way, the pin assembly 247 can pivot about the bolt 236 in a plane normal to the axial direction in response to side-ways oscillatory motion of the first sub-cam 244. The second end of the pin assembly 247 is coupled to the second sub-cam 246 at a position below the proximal connecting pin 243c. Ball joints can be provided between the first and second ends of the pin assembly 247 and the respective first and second sub-cams 244, 246 to ease relative motion between them.

In this example, the second sub-cam 246 is not driven directly by the main cam 242. Instead, the main cam 242 applies an oscillatory motion to the first sub-cam 244 which in turn causes the pin assembly 247 to pivot about the central bolt 236. The pivoting action of the pin assembly 247 causes an opposing oscillatory motion to be transferred to the second sub-cam 246 which swivels in the opposite direction to the first sub-cam 244 about its proximal connecting pin 243c.

Returning to FIGS. 2a and 2b, the first and second sub-cams 244, 246 each have a distended portion from which associated first and second extension members 248, 250 can engagably extend. The first and second extension members 248, 250 may be provided as cylinders that are laser welded to the inner surface 212 of the cutting band 202. This welding method reduces the risk of tearing the foil of the cutting band 202 because the contact area between the weld points is increased compared to other methods. Alternatively, a frictional contact or releasable coupling between the first and second extension members 248, 250 and the cutting band 202 may be sufficient in some examples. The first extension member 248 can be considered to be a drive member that provides as an oscillatory displacing force to the cutting band 202. The cutting band 202 is drawn back and forth around the first and second subassemblies 218, 220 in order to trace an oval shape. The resulting oscillatory motion of the cutting band 202 is in a range of around 4 mm. A suitable tooth width is typically half the oscillatory range and so is around 2 mm in this example.

The tool head assembly also comprises a third housing sub-assembly 240. The first, second and third housing sub-assemblies 218, 220, 240 are coupled to and held in a fixed relationship in the axial direction with the main housing 201 by a nut 234 and bolt 236 (or similar). The bolt 236 passes through a central aperture in the first, second and third housing sub-assemblies 218, 220 in the axial direction and engages with the nut 234, which is provided in a recess within the main housing 201. A spacer 238 is also provided along the axis of the bolt 236 between the first housing sub-assembly 218 and the third housing sub-assembly 240. The spacer 238 is configured to engage with retaining pins that extend from the first housing sub-assembly 218. The spacer 238 is also configured to slot into a recess in the third housing sub-assembly 240 so as to be maintained in a fixed relative position between the first housing sub-assembly 218 and the third housing sub-assembly 240.

In use, the saw is mounted to the body 201 and the driving member of the saw is coupled to the main cam 242. Oscillatory motion from the saw is transferred by the first cam sub-assembly 244 and first extension member 248 to the cutting band 202 and so imparts a back-and-forth oscillatory motion on the cutting band 202. The cutting band is held in tension during use by the rollers 222, 224 such that its cutting edge follows a cutting path defined by the first and second housing sub-assemblies 218, 220 and rollers 222, 224, which may be elliptical or oval, for example.

Figure 2D:
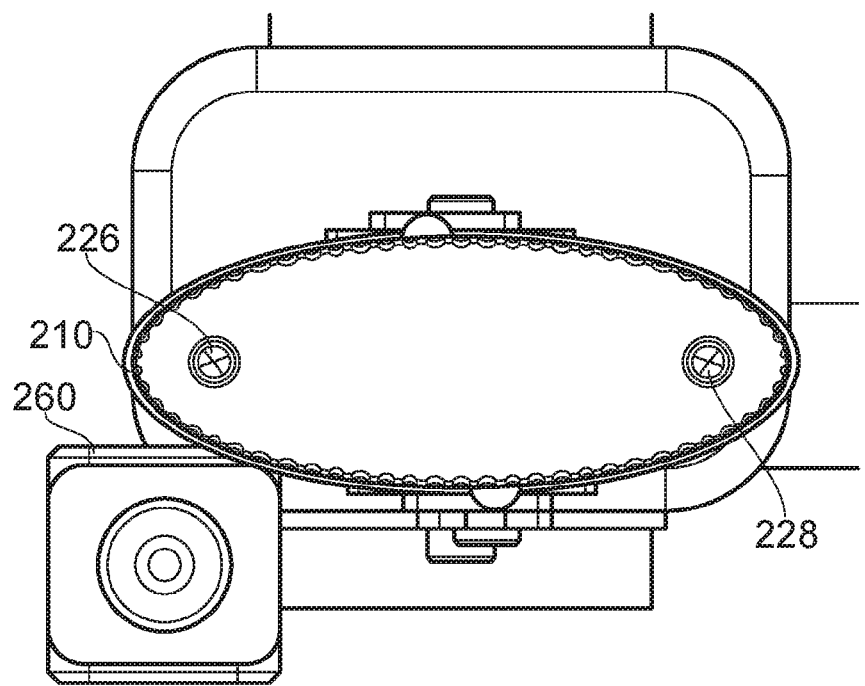
FIG. 2d illustrates a plan view of a cutting edge of the oscillating saw head assembly illustrated in FIG. 2c.

FIG. 2d illustrates a plan view of a cutting edge of the oscillating saw head assembly 200 illustrated in FIG. 2c. In this view the oval cutting path of the cutting edge 210 is shown extending around the guidance assembly comprising the first and second guidance pins 226, 228.

An accessory 260 is also mounted on the housing 201. Possible examples of accessories include a torch, camera or guide device. It will be appreciated that the accessory can also be mounted on a drill or saw driving force unit, rather than the tool head assembly 200.

FIGS. 3a and 3b illustrate exploded perspective views of a drill head assembly 300 for receiving a continuous rotational driving force.

The tool head assembly 300 comprises a main housing, or body 301a, 301b and a cutting band 302. The body 301a, 301b is configured to be attached to a drill. The body 301a, 301b is coupled to combined tension and drive members 378, 380 that provide both tension and a rotational driving force to the cutting band 202. The cutting band 302 is substantially the same as the cutting blade described previously with regard to the tool head assembly of FIGS. 2a and 2b. The cutting band 302 is wrapped around and therefore takes the shape of an inner support frame 321 that can be provided as a unitary component or using the first and second sub-assembly housings and associated components described previously. The position of the frame can be used to set the maximum cut depth of the cutting band 302.

The tool head assembly 300 also has a continuous rotational motion transfer apparatus that comprises a drive shaft 360, a first drive member 362 and a second drive member 364. Each of the drive shaft 360 and drive members 362, 364 extend in an axial direction that is normal to a cutting plane defined by the cutting edge of the cutting band 302. The drive shaft 360 extends through an opening in an end face of the main housing 301b. The first and second drive members 362, 364, or drive shafts, are disposed within the main housing 301a on opposing sides of the drive shaft 360. The first and second drive members 362, 364 are engaged with the drive shaft by an arrangement of cogs 367 such that rotation of the drive shaft 360 results in an opposing rotation of both the first and second drive members 362, 364. The first and second drive members 362, 364 each comprise a roller. The rollers 303 are provided at respective opposing ends of the drive members 362, 364 to the cogs 367. The rollers 303 are provided adjacent to, and in direct rolling contact with, the inner surface of the cutting band 302 and impart a frictional force upon the inner surface. In this example, there are therefore a plurality of drive members 362, 364 and a plurality of tension members. In fact, each drive member 362, 364 is also a tension member. The continuous rotational motion transfer apparatus can therefore be considered to be integrated with a tension imparting portion of the tool head assembly 300.

The degree of tension imparted by the drive members 362, 364 can be controlled by altering a displacement between a first housing sub-assembly 366 and a second housing sub-assembly 368. The first and second housing sub-assemblies 366, 368 are slidable along a first set of parallel rails 370 that extend within the main housing 301a orthogonal to the axial direction. The first and second housing sub-assemblies 366, 368 each comprise an aperture that extends in the axial direction and is between the first set of rails 370. The housing sub-assemblies 366, 368 also provide a guide for the first and second drive members 362, 364.

The first and second drive members 362, 364 each pass through a respective one of the first and second housing sub-assemblies 366, 368 such that the cogs 367 of the drive members 362, 364 and the rollers 303 of the drive members 362, 364 are provided on opposite sides of the sub-assemblies 366, 368. Springs are provided to bias the housing sub-assemblies 366, 368 towards one another and away from the walls of the housing 301b. A third housing sub-assembly 372 is provided along a second set of parallel rails 374 that extends within the main housing 301a orthogonal to both the axial direction and the second set of rails 374. The third housing sub-assembly 372 has a sloped surface disposed in contact with each of the first and second housing sub-assemblies 366, 368. Movement of the third housing sub-assembly 372 along the rails 374 controls the displacement between the first and second housing sub-assemblies 366, 368. A control knob 376 disposed on the outside of the main housing 301b is engaged with the third housing sub-assembly 372 using a screw thread arrangement through a wall of the main housing 301b. The control knob is configured to control the position of the third housing sub-assembly along the rails 374. In use, the user can rotate the control knob to set the displacement between the first and second housing sub-assemblies 366, 368 and accordingly set the tension imparted on the cutting band 302 by the first and second drive members 362, 364.

The tool head assembly also comprises a guidance assembly comprising a first guidance pin 378 and a second guidance pin 380. The guidance pins 378, 380 are the first portions of the assembly 300 to interact with the surface of the subject. A pointed ends of the guidance pins 378, 380 may dig into the subject to an extent and prevent lateral movement of the subject relative to the assembly 300 as the cutting band 302 is engaged. Pressing the assembly 300 onto the subject causes the guidance pins 378, 380 to retract towards the housing and allow the cutting band 302 to engage with the surface of the subject.

The first and second guidance pins 378, 380 extend from the axes of the rollers 303 of the respective first and second drive members 362, 364. The first and second guidance pins 378, 380 have retaining portions that extend normal to the pin axes. Springs are provided along the respective axes of the first and second guidance pins 378, 380 and provide a bias force on the retaining portions relative to the first and second drive members 362, 364. The effect of this bias is that the pointed end of each of the guidance pins 378, 380 retractably protrudes from the assembly 300 through the cutting plane, within the cutting band 302.

Figure 4C:
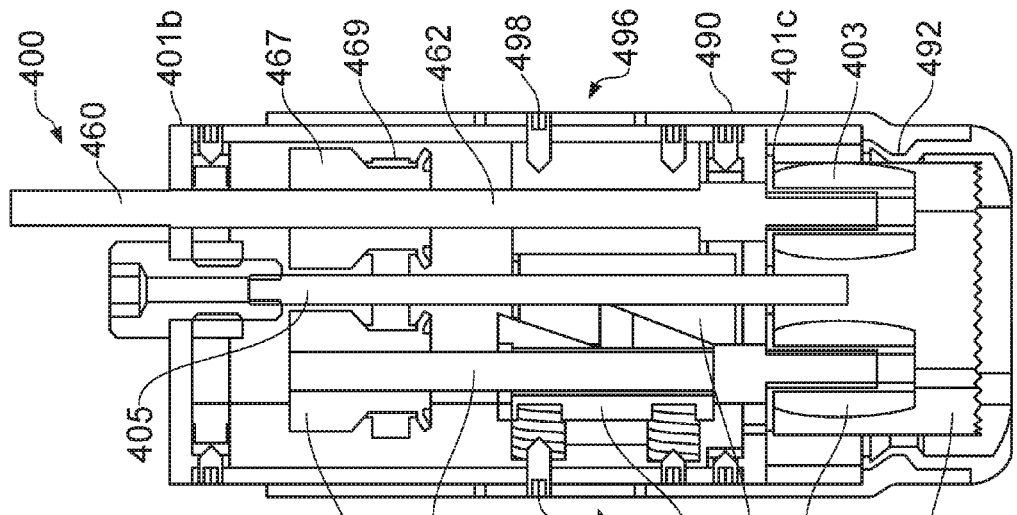
Figure 4B:
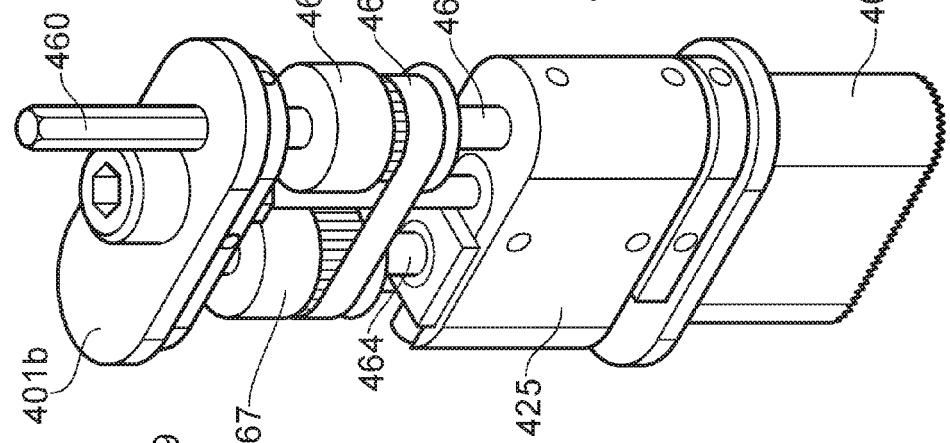
Figure 4A:
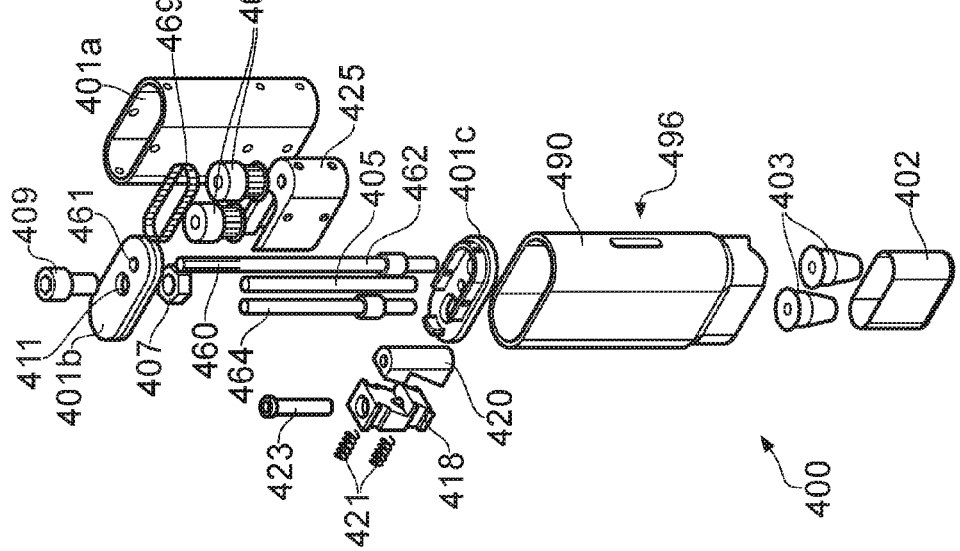
FIG. 4a illustrates an exploded perspective view of a drill head assembly for receiving an continuous rotational driving force.

FIGS. 4a, 4b and 4c illustrate views of another drill head assembly 400 for receiving a continuous rotational driving force. FIG. 4a illustrates an exploded perspective view of the drill head assembly 400. FIG. 4b illustrates a perspective view of a mechanism within the drill head assembly 400. FIG. 4c illustrates a schematic cross section taken through the drill head assembly 400.

Similarities between the drill head assembly 400 and the drill head assembly described above with reference to FIG. 3 will not, in general, be described further below. Reference numerals in the 400 series corresponding to reference numerals in the 300 series are used to refer to similar components in the arrangements of FIGS. 3 and 4.

The drill head assembly 400 has a continuous rotational motion transfer apparatus disposed within the main housing. The main housing is cylindrical and has a central portion 401a between a proximal end face 401b and a distal end face 401c.

The rotational motion transfer apparatus comprises a drive shaft 460 which extends in an axial direction and also defines a first drive member 462. The drive shaft 460 extends through an opening 461 in the proximal end face 401b of the main housing in order to receive torque from an external source, such as a drill (not shown). The rotational motion transfer apparatus also comprises a second drive member 464. The first and second drive members 462, 464 each have a drive roller, or drive cog 467. A drive belt 469 is mounted on the drive cogs 467. The drive belt 469 in this example has teeth disposed on an inner surface. The teeth are engaged with teeth of the cogs 467. The first drive member 462 is therefore coupled to the second drive member 464 by the drive belt 469 such that rotation of the drive shaft 460 results in a corresponding rotation of both the first and second drive members 462, 464.

A tension setting rod 405 extends in the axial direct from the proximal end 401a of the main housing through the distal end 401c of the main housing. The first drive member 462 and second drive member 464 are provided on opposing sides of the tension setting rod 405. A nut 407 and bolt 409 are provided to hold the tension setting rod 405 in place with respect to the proximal end 401*a* of the main housing. The tension setting rod 405 extends from an axial recess in the bolt 409. The bolt 409 passes through a second opening 411 in the proximal end 401*a* of the main housing. The bolt is engaged with a nut inserted into a recess on an inner face of the proximal end 401*a* of the main housing. Rotating the bolt 409 causes a corresponding rotation of the tension setting rod 405. As discussed below, rotation of the tension setting rod 405 with respect to the main housing can be used to move the second drive member 464 between a first position and a second position. The second drive member 464 is further away from the first drive member 462 in the first position than the second position. In the first position the cutting band 402 is held under tension for cutting the subject. In the second position, the cutting band 402 is not held under tension and so the cutting band 402 is removable when the tension member is in the second position.

First and second housing sub-assemblies 418, 420 are provided within the main housing for controlling the application of tension to the cutting band 402. The second drive member 464 passes through the first housing sub-assembly 418. The first housing sub-assembly 418 is retained in a fixed position with respect to the main housing by a bolt 423 and a collar 425, which is itself affixed to the main housing. The tension setting rod 405 passes through the second housing sub-assembly 420. Interlocking screw threads are provided on the central rod 405 and second housing sub-assembly 420 such that rotation of the central rod 405 causes a change in axial displacement between the distal end 401*c* of the main housing of the second housing sub-assembly.

Springs 421, in this example, act as biasing members that are configured to urge the first housing sub-assembly 418 to maintain contact with the second housing sub-assembly 420. The first and second housing sub-assemblies 418, 420 have interlockable wedge shaped portions. Changing a displacement of the first housing sub-assembly 418 with respect to the second housing sub-assembly 420 in the axial direction has the effect of changing the thickness at which wedge shaped portion of the second housing sub-assembly 420 contacts the wedge shaped portion of first housing sub-assembly 418. Changing the axial position of the second housing sub-assembly 420 by rotating the tension setting rod can therefore be used to control a separation between the first and second drive members 462 and so vary the tension of the cutting band.

The first and second drive members 462, 464 extend through the distal end face 401*c* of the main housing. Rollers 403 are provided on the first and second drive members 462, 464 outside of the main housing 401 in order to engage with the cutting band 402. The rollers 402 function in a similar way to those described with reference to FIG. 3.

The drill head assembly 400 has an outer sleeve 490 which extends around the main housing 401*a*. The sleeve 490 forms a handle for a user to hold the drill head assembly 400 and in some examples may be provided in an ergonomically designed shape to ease use.

The sleeve 490 has V-shaped grooves 492 that extend on either side of the cutting band 402. The grooves 492 are configured to engage with a subject (bone) around the region of the bone that the cutting band is intended to cut into. The provision of the grooves 492 assists in maintaining a fixed relationship between the bone and the drill head assembly 400 and so reduces unwanted lateral motion of the cutting band 402, which would result in damage to the bone surrounding the target area. As such the sleeve 490 can be considered to be integrally formed with a guidance assembly.

The sleeve 490 has an inner rim 494. The inner rim 494 defines a cutting path for the cutting band, together with the rollers 403, by conforming a shape of the cutting band to that of the inner rim 494.

The sleeve 490 has freedom to travel in the axial direction with respect to the central portion 401*a* of the main housing. The sleeve 490 is movable with respect to the main housing between an operating configuration, in which the cutting edge of the cutting band 402 is exposed, and a retracted configuration, in which the cutting edge is shielded from a user by the sleeve 490. FIG. 4*c* illustrates the retracted configuration in which the cutting band 402 is within the sleeve 490.

The sleeve 490 also has a slit 496 that is configured to interact with a notch 498 on the main housing 401*a*. The movement of the notch 498 within the slit may be used to define the limits of the freedom of travel of the sleeve 490 between the operating configuration and the retracted configuration. The position of the notch 498 within the slit 496 also forms a gauge for providing an indication of a level of retraction of the cutting band 402 within the sleeve 490.

Figure 5A:
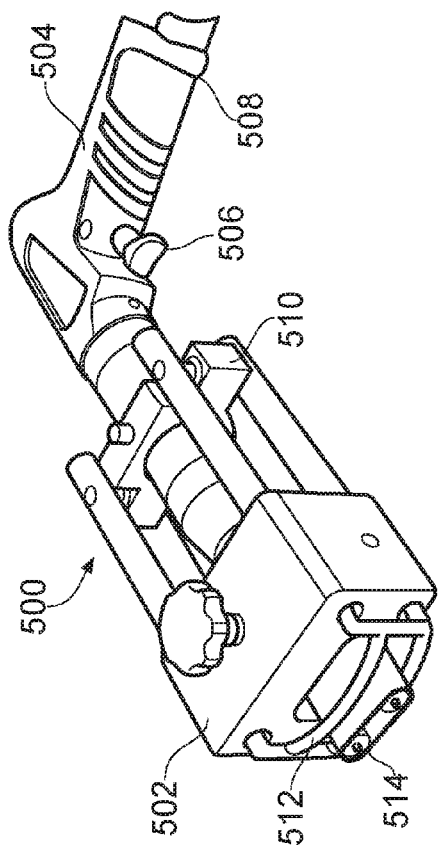
FIG. 5a illustrates a saw comprising a tool head assembly.
Figure 5C:
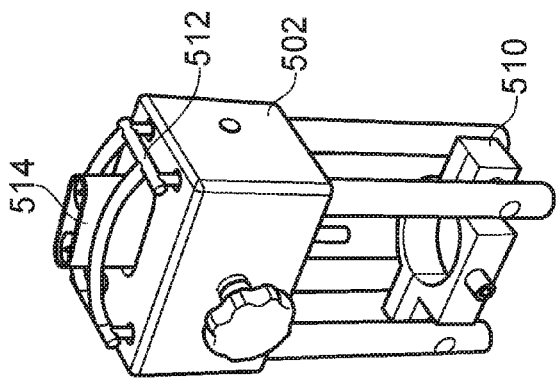
Figure 5B:
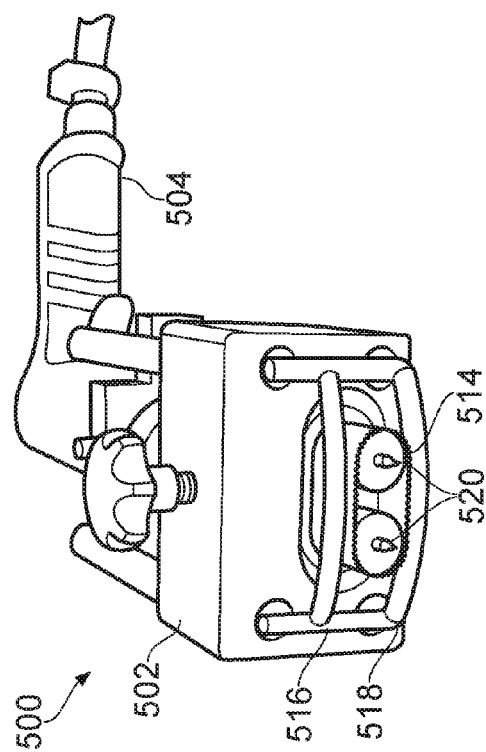

FIGS. 5*a* and 5*b* illustrates views of a saw 500 comprising a tool head assembly 502 and a hand held power tool, or driving force unit 504. The tool head assembly 502 is also shown in isolation in FIG. 5*c*.

The driving force unit 504 may be provided by a conventional hand held drill mechanism or an oscillatory saw mechanism. In this example, the driving force unit 504 is configured to provide a continuous rotational torque to the tool head assembly 502 when an operator engages a trigger 506 on a handle 508 of the driving force unit 504. The tool head assembly 502 is therefore of the continuously rotatable type described in relation to FIGS. 3*a* and 3*b*, although it will be appreciated that an oscillatory type may also be provided, subject to the necessary modifications to the driving force unit.

In addition to the features described in relation to FIGS. 3*a* and 3*b*, the tool head assembly 502 comprises a clamp portion 510 and a guide frame 512.

The clamp portion 510 can be used to firmly attach the tool head assembly 502 to the driving force unit 504 to prevent relative movement between the two during use.

The guide frame 512 can be considered to provide part of a guidance assembly and is configured to engage with a subject (bone) around the region of the bone that the cutting band 514 cuts into. The provision of the guide frame 512, in addition to the guide pins 520, assists in providing a fixed relationship between the bone and the tool head assembly 502 and so reduces unwanted lateral motion of the cutting band, which would result in damage to the bone surrounding the target area.

The structure of the guide frame 512 is shown in detail in FIG. 4*b*. The guide frame 512 has a first guide rail 516 and a second guide rail 518. The first and second guide rails 516, 518 are disposed on opposite sides of the cutting band 514 and are separated from each other by a distance that relates to the width of the bone that the tool head assembly 502 is intended to engage with. In the example shown, the first and second guide rails 516, 518 of the guide frame 512 have a fixed relative relationship, although it will be appreciated that the separation between the guide rails 516, 518 could be adaptable.

The invention claimed is:

1. A tool head assembly for a hand held tool, the assembly comprising:
a body for attaching to the hand held tool;
a continuous cutting band having a cutting edge for cutting into a subject;
at least one tension member coupled to the body and configured to hold the cutting band under tension;
at least one drive member coupled to the body and configured to rotate the cutting band with respect to the body; and
a guidance assembly for retractably engaging with the subject and maintaining a fixed lateral relationship between the cutting band and the subject.

2. The tool head assembly of claim 1 wherein the cutting edge is disposed in a cutting plane.

3. The tool head assembly of claim 1 comprising a guidance assembly for retractably engaging with the subject and maintaining a fixed lateral relationship between the cutting band and the subject.

4. The tool head assembly of claim 1 wherein the guidance assembly comprises guidance pins.

5. The tool head assembly of claim 4 wherein the pins extend from the drive member.

6. The tool head assembly of claim 1 wherein the guidance assembly comprises guide rails that extend on either side of the cutting band.

7. The tool head assembly of claim 1 wherein the guidance assembly comprises grooves that extend on either side of the cutting band.

8. The tool head assembly of claim 1 wherein the guidance assembly is configured to interact with the body to form a gauge for providing an indication of a level of retraction of the guidance assembly with respect to the body.

9. The tool head assembly of claim 8 wherein the guidance assembly is integrated with a sleeve which extends around the body.

10. The tool head assembly of claim 1 wherein the guidance assembly defines a cutting path of the cutting band.

11. The tool head assembly of claim 1 wherein the cutting band has at least one characteristic selected from a group of characteristics consisting of:
being configured to follow an oval or elliptical path;
being flexible when not under tension; and
being removable and replaceable.

12. The tool head assembly of claim 1 wherein the cutting edge has at least one characteristic selected from a group of characteristics consisting of:
being continuous;
having a thickness less than 0.2 mm;
being suitable for cutting human or animal bone;
comprising symmetrical teeth; and
being exposed in its entirety.

13. The tool head assembly of claim 1 wherein the cutting band is flexible when not under tension and at least one tension member is movable between a first position in which the cutting band is held under tension and a second position in which the band is not held under tension, wherein the cutting band is removable when the tension member is in the second position.

14. The tool head assembly of claim 1 wherein the cutting band tension member is integrated with the drive member.

15. The tool head assembly of claim 1 wherein the drive member comprises a plurality of drive members, each of which is in contact with the cutting band.

16. The tool head assembly of claim 15 comprising wherein said plurality of drive members comprises a first drive member and a second drive member, wherein the first drive member is configured to receive a torque and transfer the torque to both the second drive member and the cutting band.

17. The tool head assembly of claim 1 comprising a plurality of tension members, each comprising a roller that is engagable with, and configured to apply a force to, an inner surface of the cutting band in order to hold the cutting band in the tool head assembly.

18. The tool head assembly of claim 17 wherein the tension member is moveable between a first position in which the cutting band is held under tension and a second position in which the cutting band is not held under tension, and the cutting band is removable when the tension member is in the second position and one of the plurality of tension members is displaceable towards another of the tension member in order to relieve the force applied to the inner surface of the cutting band so that the cutting band may be removed from the tool head assembly.

19. The tool head assembly of claim 1 configured to receive force from an oscillating driving force and impart an oscillatory motion on the cutting band.

20. A saw or drill comprising the tool head assembly of claim 1 wherein the drive member is configured to receive torque from a driving force unit of the saw or drill.

* * * * *